United States Patent [19]

Yamaguchi et al.

[11] 4,295,581
[45] Oct. 20, 1981

[54] INSECTICIDAL AEROSOL FORMULATION HAVING A LIQUIFIED PETROLEUM GAS PROPELLANT

[75] Inventors: Takashi Yamaguchi, Nishinomiya; Yoshitoshi Okuno, Toyonaka; Chuji Hirose, Takarazuka, all of Japan

[73] Assignee: Sumitomo Chemical Company, Limited, Osaka, Japan

[21] Appl. No.: 133,600

[22] Filed: Mar. 24, 1980

Related U.S. Application Data

[63] Continuation of Ser. No. 857,801, Dec. 5, 1977.

[30] Foreign Application Priority Data

Dec. 9, 1976 [JP] Japan .................................. 51-148426

[51] Int. Cl.$^3$ ............................................. B65D 83/14
[52] U.S. Cl. ................................. 222/192; 222/402.18
[58] Field of Search ....................... 222/402.18, 192, 1

[56] References Cited

U.S. PATENT DOCUMENTS 3,137,416  6/1964  Shepherd et al. .................... 222/192
3,303,091  2/1967  Mailander et al. ......... 222/402.18 X
3,544,258  12/1970  Presant et al. ............. 222/402.18 X

FOREIGN PATENT DOCUMENTS 51-70826  6/1976  Japan ...................... 222/402.18 UX

OTHER PUBLICATIONS

Sciarra et al., *The Science and Technology of Aerosol Packaging*, Wiley & Sons, pbl., 1974, pp. 459 & 482.
Johnsen, "Aerosol Age", Dee 1975, pp. 36–38 & 40.

*Primary Examiner*—David A. Scherbel
*Attorney, Agent, or Firm*—Stevens, Davis, Miller & Mosher

[57]  ABSTRACT

An insecticidal aerosol formulation comprising a pressure-proof container equipped with a valve having a housing, button, stem and vapor tap, filled with a solution of an active ingredient in kerosenes having a boiling point of 180°–260° C. and a liquified petroleum gas as a propellant.

1 Claim, 1 Drawing Figure

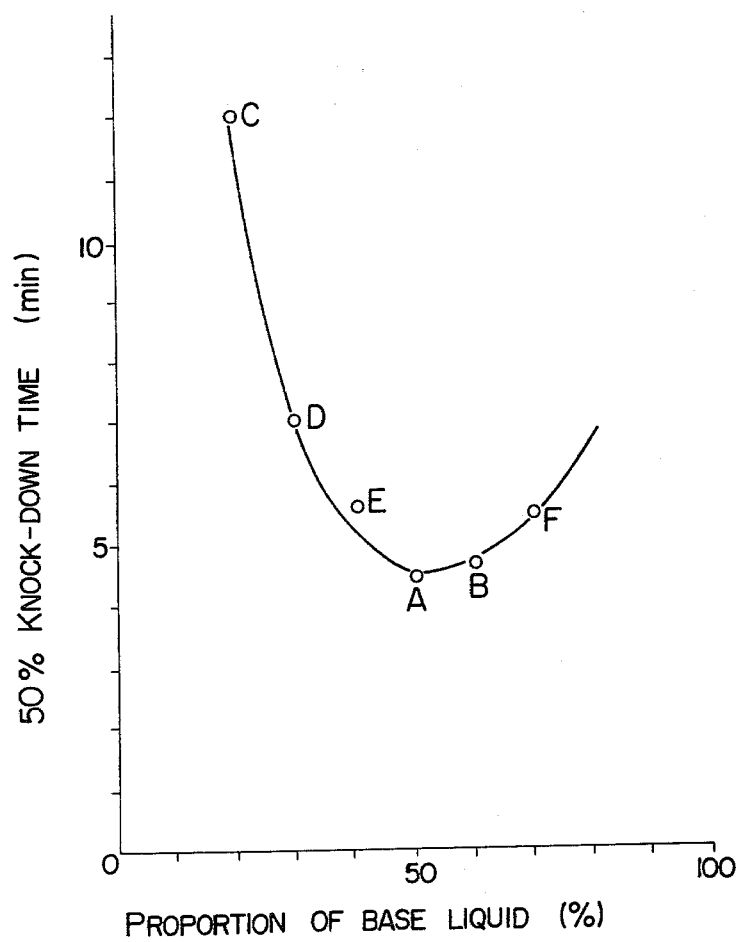

INSECTICIDAL AEROSOL FORMULATION HAVING A LIQUIFIED PETROLEUM GAS PROPELLANT

This is a continuation of application Ser. No. 857,801 filed Dec. 5, 1977.

The present invention relates to an insecticidal aerosol formulation characterized in that said formulation contains, as an essential active ingredient, one or more materials selected from the group consisting of pyrethroid type insecticides, for example, allethrin, phthalthrin, resmethrin, phenothrin, permethrin and isomers thereof, and natural pyrethrin, and are effective for promoting a controlling efficiency and poor in inflammability.

Insecticidal aerosol formulations mainly comprise an active ingredient, solvent, propellant, valve system and container. As the active ingredient, pyrethroid type insecticides low in toxicity and excellent in rapid effectiveness are in use. Organo-phosphorus compounds, carbamate compounds or synergists are sometimes used in combination with pyrethroid type insecticides according to the purposes of use. It is needless to say that the proportion of active ingredient and, if the active ingredient is a mixture, the mixing ratio are very important.

As the solvent, kerosenes are commonly used. The kerosenes are solvents having wide ranges of boiling point and other physical properties, and it may be considered that there exist desirable ranges in terms of insecticidal effect. Consequently, there is room for further investigation. As an auxiliary solvent, methylene chloride, methylchloroform, xylene or the like is sometimes used in combination.

As the propellant for the conventional aerosol formulation, freons, dimethyl ether, liquefied petroleum gases and mixtures thereof are commonly used. Recently, the use of carbon dioxide gas has been examined again, but at the present time the gas is only used for aerosols for the purpose of residual spraying and is not practically used for aerosols for the purpose of space spraying.

Freons are a very important propellant which satisfies all the requirements of a propellant for aerosols. But, recently, the toxicity problem which originates from air pollution and the ozone layer destruction by freons is under lively discussion particularly in America. At the present time, the use of freons is not completely prohibited, but it is important to take this opportunity of searching for a substitute for freons. From this standpoint, many of the insecticidal aerosol formulation which are presently marketed in Japan, contain not freons but a mixture of dimethyl ether and a liquefied petroleum gas as a propellant. Insecticidal aerosol formulations containing a liquefied petroleum gas alone as a propellant are regarded as more favorable than those containing other propellants in terms of cost and toxicity, but they are regarded as impossible in terms of danger (inflammability). But the advantages of the liquefied petroleum gas are too attractive to give up, and therefore the application of the gas to insecticidal aerosol formulation is an important subject of study.

As to the valve system, the number of systems is limitless, considering the combinations of the orifice diameters of the parts constituting the system. But, the number of the combinations suitable for aerosols having a definite composition is limited and, when the insecticidal effect and the standard of inflammability are taken into account, the number is further limited. In any case, the selection of the combination is very important.

Since the purpose of insecticidal aerosol formulations is to control harmful insects, the proper selection of the quantity and quality of active ingredients is most important. The matter of second importance is to develop such a formulation that makes the effect of active ingredient highest, in other words, that produces the highest effect using a definite amount of active ingredient, or that produces a definite effect using the least possible amount of active ingredient.

At the present time, however, the composition and valve system of insecticidal aerosol formulations is generally only determined by investigation of the physical and chemical aspects such as inner pressure, inflammability, delivery rate, spray pattern, aerosol particle size and stability of active ingredient. And, it is not too much to say that the formulation is scarcely studied on the basis of the relationship between insecticidal effect and formulation.

Believing that a normal formulation could be found by overcoming the drawbacks of the study of this old type, the inventors studied the aerosol formulation containing a liquefied petroleum gas alone as a propellant by carefully selecting the kind of solvent, the proportion of solvent to liquefied petroleum gas and the valve system. In practicing this selection, evaluation was primarily made on the basis of insecticidal activity and at the same time Notice 557 of the Japanese High Pressure Gas Control Law of the Ministry of International Trade and Industry, was also taken into account. As a result, the inventors found a novel formulation which is remarkably superior in insecticidal activity and is not inferior in physical properties to the conventional aerosol insecticides, and confirmed that this is very important socially and economically. Thus, the inventors attained the present invention.

That is, the present insecticidal aerosol formulation of high controlling efficiency comprises filling a pressure-proof container equipped with a valve system comprising a housing, button, stem and vapor tap, the orifice diameters of which are 0.46 to 0.64 mm, 0.33 to 0.41 mm, 0.33 to 0.41 mm and 0.33 to 0.41 mm, respectively, with a solution of the active ingredient in kerosenes having a boiling point of 180° C. to 260° C. and a propellant comprising a liquefied petroleum gas alone, the volume ratio of said solution to said propellant being 50:50 to 60:40.

The FIGURE is a graphical explanation of the test results shown in Example 2, as more fully described hereinafter.

As the petroleums used in the present invention, there may be given, for example, Isopar M and L (both are a trade name). As the liquefied petroleum gas, there may be given, for example, a propane/n-butane/iso-butane mixture (50:14:36).

The requirements of practical insecticidal aerosol formulation are the rapidity of knock-down effect (rapid effectiveness) and the certainty of control. In the scope of the present invention, the aerosol insecticides containing a definite active ingredient in a definite amount sufficiently satisfy these requirements.

On the other hand, when the boiling point of petroleums is outside the scope of the present invention, for example, less than 180° C., the petroleums are low in viscosity and surface tension and further, are easily volatile so that aerosol particles are small. Consequently, the period during which the particles stay in the air becomes long with an enhanced persistence of the effect. But both the rapid effectiveness and the certainty of control are inferior to those of the present invention, because the particles are too small to attach enough to insect bodies. Contrary to this, the solvents having a boiling point of higher than 260° C. produce large aerosol particles which are very effective in the direct action on insect bodies but is too short in the staying period. Therefore such an insecticidal aerosol formulation is not satisfactory for the purpose of space spraying.

The same tendency was also observed when the ratio of a base liquid (a solution of active ingredient in a solvent) to liquefied petroleum gas was varied under a definite inner pressure. That is, when the ratio of gas was larger than that of the present invention, the rapid effectiveness was particularly unsatifactory, while when the ratio of liquid was larger than the ratio of the present invention, the certainty of control was particularly insufficient.

Generally, it is said that the smaller the aerosol particles the better the results. But, by the study of the inventors, it became clear that the aerosol particles should have a moderate size in order to obtain aerosols having a high controlling effect.

Also, the aerosol particle size depends upon the combination of the orifice diameters of the parts constituting the valve system, and therefore the controlling effect is largely influenced.

The inventors examined the relationships between the insecticidal effect and a number of combinations of the orifice diameters of the parts, and as a result found that the valves of the following combinations are preferable in terms of the effect:

1. Stem orifice diameter≦vapor tap orifice diameter≦button orifice diameter<housing orifice diameter
2. Stem orifice diameter≦button orifice diameter<housing orifice diameter (no vapor tap)

On the other hand, as a result of the inflammability test using ten-odd kinds of valve systems having the aforesaid orders of orifice diameters, it was found that the preferred valves among the first group are such that the orifice diameters of the stem, vapor tap, button and housing are 0.33 to 0.41 mm, 0.33 to 0.41 mm, 0.33 to 0.41 mm and 0.46 to 0.64 mm, respectively, and that all the valves having larger orifice diameters do not pass the standard of inflammability. Further, it was found that the valves of the second group do not pass the standard independently of the size of orifice diameter.

As described above, a preferred combination of orifice diameter is limited to a very narrow range from the standpoint of insecticidal activity, and the combination is further limited when the inflammability is taken into account.

Although oil-based aerosol formulations containing a liquefied petroleum gas alone as a propellant have so far been regarded as impossible in terms of inflammability, it became clear by the inventors that low inflammable aerosols are possible within a severely limited range, even though the aerosols use a liquefied petroleum gas alone as a propellant.

Next, the example of pyrethroid type insecticide according to the present invention will be shown hereinafter.

| Abbreviation or common name | Chemical name |
|---|---|
| 1. Phthalthrin | 3,4,5,6-Tetrahydropthalimido-(±)cis,trans-chrysanthemate |
| 2. Resmethrin | 5-Benzyl-3-furylmethyl-(±)cis,trans-chrysanthemate |
| 3. d-Resmethrin | 5-Benzyl-3-furylmethyl-(+)-cis,trans-chrysanthemate |
| 4. d-trans-Resmethrin | 5-Benzyl-3-furylmethyl-(+)-trans-chrysanthemate |
| 5. d-Phenothrin | 3-Phenoxybenzyl-(+)cis,trans-chrysanthemate |
| 6. Allethrin | (±)-2-Allyl-3-methylcyclopent-2-ene-7-one-4-yl-(±)cis,trans-chrysanthemate |
| 7. (±)-Allethrolone-(+)cis,trans-chrysanthemate | (±)-2-Allyl-3-methylcyclopent-2-ene-1-one-4-yl-(+)cis,trans-chrysanthemate |
| 8. (±)-Allethrolone-(+)-trans-chrysanthemate | (±)-2-Allyl-3-methylcyclopent-2-ene-1-one-4-yl-(+)trans-chrysanthemate |
| 9. (+)-Allethrolone-(+)-cis,trans-chrysanthemate | (+)-2-Allyl-3-methylcyclopent-2-ene-1-one-4-yl-(+)cis,trans-chrysanthemate |
| 10. (+)-Allethrolone-(+)trans-chrysanthemate | (+)-2-Allyl-3-methylcyclopent-2-ene-1-one-4-yl-(+)trans-chrysanthemate |
| 11. Permethrin | 3-Phenoxybenzyl-(±)cis,trans-2,2-dimethyl-3-(2,2-dichlorovinyl)cyclopropanecarboxylate |

The present invention will be illustrated in detail with reference to the following examples.

EXAMPLE 1

0.6 g of phthalthrin and 0.3 g of d-phenothrin were dissolved in 150 ml of Isopar M (trade name, boiling point 207°–257° C.), and the solution was placed in an aerosol container. Thereafter, 150 ml of a liquefied petroleum gas was charged into the container by the usual manner to obtain 300 ml of the insecticidal aerosol formulation of the present invention (sample A).

In the same manner as above, aerosols B and C as a control were obtained using Isopar E (trade name, boiling point 115° to 145° C.) and Ondina oil (trade name, boiling point 320° to 360° C.), respectively.

Insecticidal activity tests were carried out as follows using these samples, and the results as shown in Table 1 were obtained.

One hundred house-fly adults (*Musca domestica*) were liberated in a (6 ft)$^3$ Peet Grady's chamber (6 ft equals to about 180 cm). After 5 minutes, 650±100 mg of each sample was sprayed into the chamber and the number of knocked-down house-flies was counted with the lapes of time. All the house-flies tested were then collected between 15 minutes and 20 minutes after spraying while exhausting the air from the chamber, transferred into a recovery container and fed to observe the mortality after 24 hours.

This test was repeated five times to obtain the means values of the KT$_{50}$ (a median knock-down time) and mortality.

TABLE 1

| Sample | | Knock-down ratio (%) | | | | KT$_{50}$ (min) | Mortality (%) |
|---|---|---|---|---|---|---|---|
| | | 3 min | 5 min | 10 min | 15 min | | |
| Present example | A | 34 | 50 | 74 | 86 | 4.9 | 95 |
| Control | B | 5 | 20 | 65 | 81 | 8.1 | 78 |
| | C | 36 | 43 | 56 | 64 | 6.9 | 71 |

As is clearly shown in Table 1, the sample A of the present invention is very superior in the knock-down effects immediately after spraying and 15 minutes after spraying, and in the lethal effect. While the control B is fairly good in the knock-down effect 15 minutes after spraying, it is inferior in the knock-down effect immediately after spraying and in the lethal effect. The control C is good in the knock-down effect immediately after spraying, but the knock-down ratio is not increased in the latter half of the test period and the lethal effet is also low.

EXAMPLE 2

0.6 g of phthalthrin and 0.3 g of d-phenothrin were dissolved in 150 ml and 180 ml of Isopar M, respectively, and each solution was placed in an aerosol container. Thereafter, a liquefied petroleum gas was charged into each container to obtain 300 ml of the aerosol of the present invention (samples A and B).

The above active ingredients were dissolved in 60 ml, 90 ml, 120 ml and 210 ml of Isopar M, respectively. Thereafter, the procedure was carried out in the same manner as above to obtain 300 ml of an aerosol as a control (samples C, D, E and F).

Insecticidal activity tests were carried out in the same manner as in Example 1 using these samples, and the results as shown in the FIGURE were obtained.

The FIGURE is the graphical explanation of the test results (insecticidal effect) in Example 2. The ordinate shows a time for 50% of the tested insects to be knocked down ($KT_{50}$, unit min.), and the abscissa shows the proportion (%) of the base liquid in the aerosol.

The samples A and B of the present invention show small values of $KT_{50}$ as compared with those of other ones, which means that the samples A and B are superior in the rapid effectiveness.

EXAMPLE 3

0.6 g of phthalthrin and 0.3 g of d-phenothrin were dissolved in Isopar M to make up to 150 ml of total volume. This solution was placed in aerosol containers equipped with a valve of different orifice diameter (one valve; button orifice diameter 0.35 mm, stem orifice diameter 0.33 mm, housing orifice diameter 0.64 mm, vapor tap orifice diameter 0.33 mm: another valve; 0.41 mm, 0.41 mm, 0.64 mm, 0.41 mm in the same order as above). Thereafter, 150 ml of a liquefied petroleum gas was charged into each container to obtain 300 ml of the aerosol of the present invention (samples A and B).

In the same manner as above, aerosols as a control were obtained by placing the above base liquid in aerosol containers equipped with a valve of different orifice diameter (one valve; orifice diameters of button, stem, housing and vapor tap were 0.35 mm, 0.33 mm, 0.46 mm and 0.0 mm (no orifice) respectively: another valve; 0.35 mm, 0.33 mm, 0.64 mm, 0.46 mm in the same order as above) and charging a liquefied petroleum gas in the containers (samples C and D).

Insecticidal activity tests were carried out in the same manner as in Example 1 using these samples. At the same time, the inflammability of the samples were measured according to Notice 557 of the Japanese High Pressure Gas Control Law of the Ministry of International Trade and Industry. Thus, the results as shown in Table 2 were obtained.

TABLE 2

| Sample | | Knock-down ratio (%) | | | | $KT_{50}$ (min) | Mortality (%) | Judgement of inflammability |
|---|---|---|---|---|---|---|---|---|
| | | 3 min | 5 min | 10 min | 15 min | | | |
| Present example | A | 34 | 52 | 75 | 87 | 4.7 | 94 | O |
| | B | 31 | 48 | 76 | 85 | 4.9 | 96 | O |
| Control | C | 35 | 48 | 70 | 83 | 5.2 | 91 | X |
| | D | 19 | 36 | 64 | 76 | 7.3 | 80 | O |

The samples A and B of the present invention are good in both the insecticidal effect and the inflammability. While the control C is good in the insecticidal effect but is unsatisfactory in the inflammability, and the control D is good in the inflammability but unsatisfactory in the insecticidal effect.

EXAMPLE 4

A solution of 0.6 g of tetramethrin in 150 ml of Isopar M was placed in an aerosol container which was then equipped with a valve and charged with a liquefied petroleum gas by the usual method. Thus, 300 ml of the aerosol of the present invention was obtained (sample A).

In the same manner as above, 300 ml each of the present aerosols containing the following active ingredients was obtained: Tetramethrin 0.6 g+d-phenothrin 0.3 g (sample B); tetramethrin 0.6 g+resmethrin 0.3 g (sample C); tetramethrin 0.6 g+piperonylbutoxide 3.0 g (sample D); tetramethrin 0.3 g+(±)-allethrolone-(+)-cis,trans-chrysanthemate 0.3 g+d-phenothrin 0.3 g (sample E); (±)-allethrolone-(+)-trans-chrysanthemate 0.6 g+resmethrin 0.3 g (sample F); (+)-allethrolone-(+)-trans-chrysanthemate 0.3 g+d-phenothrin 0.3 g (sample G); and natural pyrethrin 0.6 g+piperolybutoxide 3.0 g (sample H).

Separately from this, a solution of 0.6 g of tetramethrin in 90 ml of Isopar M was placed in an aerosol container which was then equipped with a valve and charged with 210 ml of freon 11/freon 12 (30:70) by the usual method. Thus, 300 ml of an aerosol as a control was obtained (sample A').

In the same manner as above, 300 ml each of the control aerosols corresponding to the samples B to H was obtained (samples B' to H').

Insecticidal activity tests were carried out in the same manner as in Example 1 using these samples, and the results as shown in Table 3 were obtained. In the tests of the control aerosols, the amount of sample sprayed was fixed at about 1200 mg in order to make the amount of active ingredient sprayed constant.

TABLE 3

| Present example | | | Control | | |
|---|---|---|---|---|---|
| Sample | $KT_{50}$ (min) | Mortality (%) | Sample | $KT_{50}$ (min) | Mortality (%) |
| A | 5.2 | 49 | A' | 7.2 | 32 |
| B | 4.6 | 92 | B' | 6.7 | 86 |
| C | 4.6 | 90 | C' | 6.6 | 85 |
| D | 4.5 | 87 | D' | 6.4 | 79 |
| E | 4.2 | 98 | E' | 6.4 | 82 |
| F | 4.6 | 92 | F' | 7.4 | 86 |
| G | 4.5 | 94 | G' | 6.0 | 86 |
| H | 4.9 | 92 | H' | 6.5 | 87 |

The test results show that, in any case of the above active ingredients, the aerosols according to the present invention have a higher insecticidal effect than the aerosols as a control.

EXAMPLE 5

Three commercially available insecticidal aerosol formulations were analyzed for active ingredients and contents thereof. The results were as follows:

| Commercial product A | Tetramethrin | 0.05% |
|---|---|---|
| | Allethrin | 0.05% |
| | Natural pyrethrin | 0.05% |
| | Synepirin 500* | 0.8% |
| Commercial product B | Tetramethrin | 0.142% |
| | Resmethrin | 0.023% |
| | S-421* | 0.463% |
| Commercial product C | Tetramethrin | 0.1% |
| | Allethrin | 0.14% |
| | Piperonylbutoxide* | 0.25% |
| | Synepirin 500* | 0.57% |

*Synergist

Aerosols D, E and F containing the same amounts of the same active ingredients as in the commercial products A, B and C, respectively, were prepared according to the method of the present invention. The insecticidal activity tests were carried out in the same manner as in Example 1. Thus, the results as shown in Table 4 were obtained.

TABLE 4

| Sample | | Knock-down ratio (%) (min) | | | | $KT_{50}$ (min) | Mortality (%) | Relative effect* | |
|---|---|---|---|---|---|---|---|---|---|
| | | 5 | 10 | 15 | 20 | | | $KT_{50}$ | Mortality |
| Commercial product | A | 16 | 33 | 46 | 52 | 17.5 | 47 | 1.21 | 1.23 |
| Present example | D | 19 | 37 | 52 | 60 | 14.5 | 58 | | |
| Commercial product | B | 22 | 45 | 61 | 68 | 11.5 | 65 | 1.34 | 1.18 |
| Present example | E | 32 | 55 | 70 | 77 | 8.6 | 77 | | |
| Commercial product | C | 27 | 52 | 67 | 74 | 9.6 | 64 | 1.30 | 1.20 |
| Present example | F | 35 | 63 | 76 | 83 | 7.4 | 77 | | |

*$KT_{50}$: Commercial product/present example
Mortality: Present example/commercial product The results show that the insecticidal aerosol formulation according to the present invention exhibits above 20 to 30% higher insecticidal effects than the commercial products having the same contents of active ingredient.

What is claimed is:

1. An insecticidal aerosol formulation comprising a pressure-proof container equipped with a valve having a housing orifice of 0.46–0.64 mm in diameter, button, stem and vapor tap orifices of 0.33–0.41 mm in diameter wherein the stem orifice diameter≦vapor tap orifice diameter≦button orifice diameter, filled with a base liquid consisting essentially of at least one pyrethroid type insecticide dissolved in kerosene having a boiling point of 180° to 260° C. and a propellant consisting essentially of a liquified petroleum gas wherein the volume ratio of the base liquid to the liquified petroleum gas is 50:50 to 60:40.

* * * * *